United States Patent [19]
Lix et al.

[11] Patent Number: 5,203,677
[45] Date of Patent: Apr. 20, 1993

[54] SYSTEM AND METHOD FOR ANALYZING GRAVITY OF USED MOTOR OIL

[76] Inventors: Terry J. Lix, 3506 Willowlake La., Enid, Okla. 73703; Michael W. McCarty, 3610 Faulkner Dr., Rowlett, Tex. 75088

[21] Appl. No.: 822,587
[22] Filed: Jan. 17, 1990
[51] Int. Cl.⁵ .................. F04B 49/06; F04B 49/04
[52] U.S. Cl. ........................... 417/12; 417/18; 417/40; 417/44; 417/53; 417/63; 210/96.1; 137/566; 137/571
[58] Field of Search ............ 417/12, 18, 36, 40, 417/44, 53, 63; 210/96.1; 137/566, 571

[56] References Cited

U.S. PATENT DOCUMENTS

| | | |
|---|---|---|
| 3,029,898 | 4/1962 | Fraser . |
| 4,248,599 | 2/1981 | Mommesin et al. . |
| 4,420,023 | 12/1983 | Cislak . |
| 4,548,088 | 10/1985 | Hood, Jr. . |
| 4,629,398 | 12/1986 | Cahalan ........................... 417/40 |
| 4,997,003 | 3/1991 | Brennan . |
| 5,002,154 | 3/1991 | Chen . |
| 5,028,212 | 7/1991 | Brophey et al. ................. 417/36 |

*Primary Examiner*—Richard A. Bertsch
*Assistant Examiner*—David W. Scheuermann
*Attorney, Agent, or Firm*—Ross, Howison, Clapp & Korn

[57] ABSTRACT

A system and method for analyzing and collecting fluids for recycling or other disposal, such as used motor oil, by determining whether the liquid has a specific gravity falling within a predetermined range, selectively activating a pump cycle to transfer motor oil exhibiting a specific gravity within the predetermined range to a holding tank for environmentally safe storage until transportation to an appropriate recycling or other disposal center.

17 Claims, 2 Drawing Sheets

SYSTEM AND METHOD FOR ANALYZING GRAVITY OF USED MOTOR OIL

TECHNICAL FIELD

This invention relates to the collection of fluids for recycling or other disposal, and more particularly, to a system and method for determining whether the specific gravity of used motor oil is within a predetermined range and for collecting unadulterated used motor oil suitable for recycling.

BACKGROUND OF THE INVENTION

In response to public concern for energy conservation, and the health and safety of its citizens, many states have either implemented or are considering the implementation of statutes and regulations controlling the disposal of used motor oil and prohibiting improper disposal practices. Service stations, commercial oil changing businesses, fleet operators and individuals who personally change the motor oil in their automobiles, lawnmowers, snow-blowers, tractors and other household and farming equipment with internal combustion engines will now be required to dispose of used motor oil in an environmentally acceptable manner.

Previously, access to convenient collection facilities has been limited. Faced with the inconvenience of distant industrial collection centers, unregulated consumers have improperly disposed of used motor oil by releasing the oil onto the ground or in nearby landfills, sewers, septic tanks, and surface or ground waters.

It is anticipated that fleet operators, service stations and other businesses that change motor oil for the public and similar enterprises will now have an immediate need for a system for collecting and holding such oil until aggregate amounts can be transferred to a recycling center for proper reclamation or refinement. The owner or operator of a used oil collection system will need a means for detecting whether or not the consumer's used motor oil has been contaminated with foreign substances such as hazardous wastes, polychlorinated biphenyls (PCBs), or other harmful substances before placement of the oil in a holding tank. For this reason, a system and method for identifying and collecting unadulterated recyclable motor oil are needed.

SUMMARY OF THE INVENTION

According to the present invention, a system and method are provided for analyzing and collecting a liquid, preferably used motor oil, from a receptacle or container for subsequent recycling. Use of the invention disclosed herein will enable the owner or operator of a collection center to identify recyclable used motor oil before acceptance from the consumer and placement in a holding tank.

According to a preferred embodiment of the invention, a system is provided that comprises means for determining whether used motor oil in a receptacle or container has a specific gravity (preferably API gravity) falling within a predetermined range, means for providing communication between the receptacle and holding tank, means to transfer motor oil through the communication means, and means for selectively activating a pump for a predetermined interval to transfer motor oil exhibiting an API gravity within the predetermined range into a holding tank.

According to a preferred embodiment of the invention, a timer means is provided to control the pumping interval. According to another preferred embodiment of the invention, means are provided to deactivate the pump once the holding tank is full. According to another preferred embodiment of the invention, means are provided for transferring collected oil from the holding tank into another receptacle for transporting the used motor oil to an appropriate recycling center.

According to another preferred embodiment of the invention, a method for identifying the specific gravity of motor oil is provided that comprises the steps of inserting a gravity probe into a consumer's receptacle of used motor oil, determining whether the oil has an API gravity within a predetermined range, selectively activating a pump cycle for transferring recyclable oil exhibiting a specific gravity within a predetermined range into a holding tank, using a timer to control the pump cycle, repeating the pump cycle until the consumer's receptacle is empty, deactivating the pump cycle once the holding tank is full, storing the collected oil in an environmentally safe manner, and optionally, transferring the oil from the holding tank to another location.

BRIEF DESCRIPTION OF THE DRAWINGS

The system and method of the invention are further described and explained in relation to the following figures of the drawings wherein.

DESCRIPTION OF THE PREFERRED EMBODIMENTS

Figure 1:
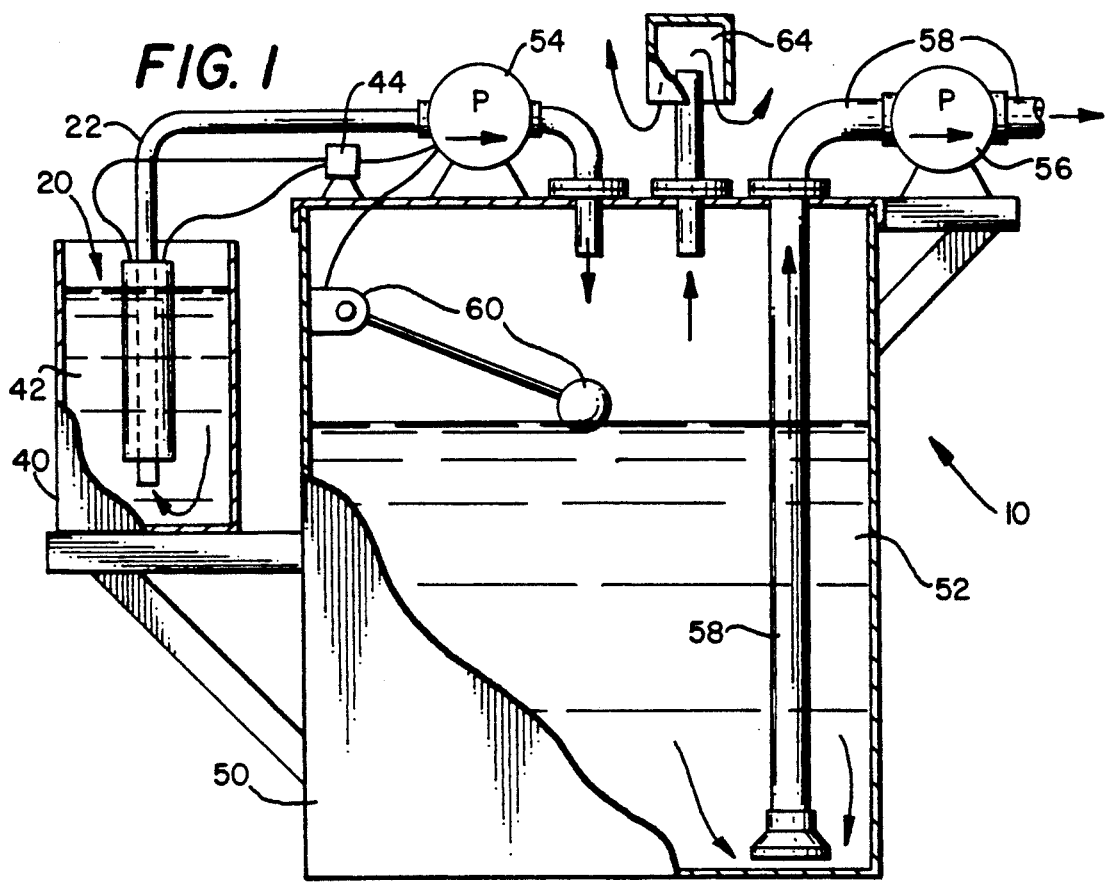
FIG. 1 is a schematic elevation view, partially in section, depicting the structure and relative placement of apparatus preferred for use in the system of the invention.

Referring to FIG. 1, system 10 of the invention preferably comprises an analyzer switch assembly 20, holding tank 50, withdrawal conduit 22, withdrawal pump 54, and timer 44. As shown in FIG. operation of the preferred embodiment begins when analyzer switch assembly 20 is placed into customer receptacle 40, fully immersing probe 29 in liquid 42. If the specific gravity of liquid 42 is within the predetermined range, analyzer switch assembly 20 activates timer 44 and pump 54, enabling pump 54 to 10 suction liquid 42 through conduit 22 into holding tank 50. Once holding tank 50 has reached its maximum capacity, float switch 60 deactivates pump 54 and liquid 52 is stored until it is transferred to another location by optional use of discharge pump 56 and suction conduit 58.

Figure 2:
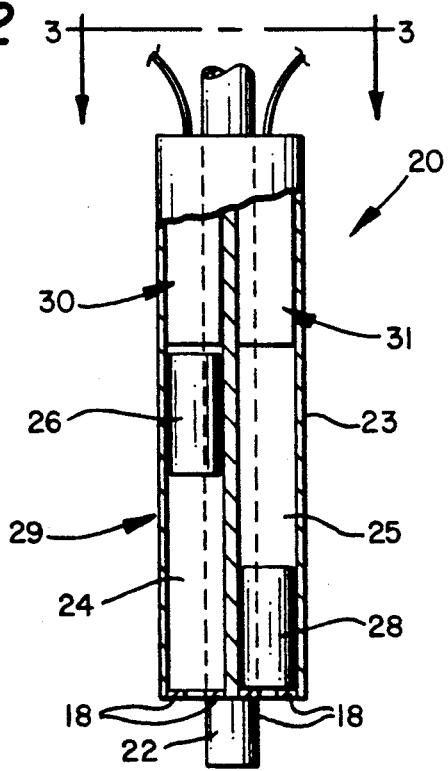
FIG. 2 is an enlarged elevation view, partially in section, depicting in greater detail the analyzer switch assembly of FIG. 1.
Figure 3:
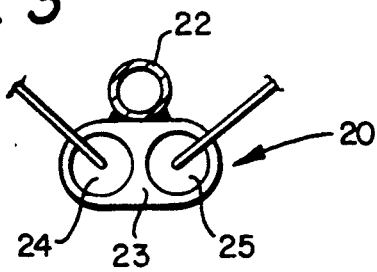
FIG. 3 is a plan view of the analyzer switch assembly taken along line 3—3 of FIG. 2.

Referring to FIGS. 2 and 3, analyzer switch assembly 20 preferably comprises a flexible withdrawal conduit 22, housing 23 with bores 24, 25, low gravity float 26, high gravity float 28, and proximity switches 30, 31. Conduit 22 and housing 23 are preferably made out of an oil resistant material. In its preferred embodiment, bores 24, 25 are formed in a single piece of extruded bar stock made of a thermoplastic material resistant to degradation by hydrocarbons. It will be understood and appreciated, however, that various other materials of construction can be utilized. Regardless of the configuration chosen, best results are achieved when the material for conduit 22 is flexible.

Figure 4:
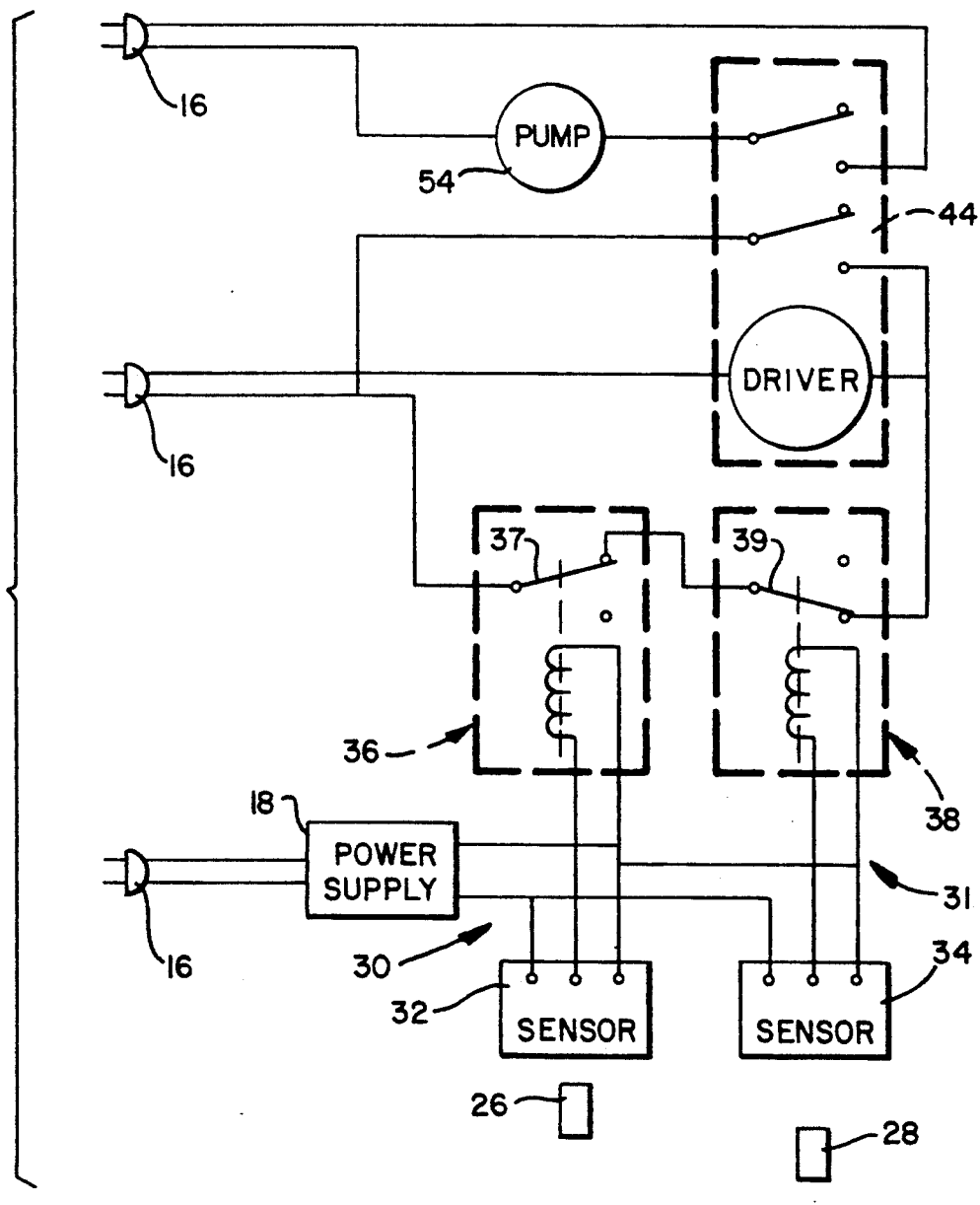
FIG. 4 is a schematic diagram illustrating a preferred electrical circuit for controlling operation of the subject system.

Referring to FIGS. 2 and 4, proximity switches 30, 31 preferably each comprise a sensor and a relay. Switches 30, 31 comprise proximity sensors 32, 34 and relays 36, 38. In a preferred embodiment, proximity switches 30, 31 are cylindrical self-tapping threaded assemblies that are inserted into bores 24, 25 of housing 23. In an alternative embodiment, smooth sided switch assemblies 30, 31 may be fastened within bores 24, 25 by using an oil resistant adhesive such as cement or epoxy.

As shown in FIGS. 2 and 4, proximity sensors 32, 34 are connected to a DC power supply 18 and AC source 16 with their respective relays 36, 38 connected in series. Internal gate 37 of relay 36 is preset in a normally open position and internal gate 39 of relay 38 is preset in a normally closed position. When the analyzer switch assembly 20 is not in use, gravity floats 26, 28 rest at the bottom of housing 23.

Gravity floats 26, 28 can be constructed from any material or combination of materials provided they compromise a metal portion and have an average density permitting flotation in a liquid having a desired specific gravity. In a preferred embodiment where the liquid to be analyzed and collected is used motor oil, gravity floats 26, 28 are constructed of material designed to float in oil within the API gravity range of 24 to 27.5 degrees, respectively. In a preferred embodiment, floats 26, 28 are prevented from falling out the bottom of bores 24, 25 by shoulders 18 or by other means such as cross pins inserted through the bottom of housing 23.

Referring to FIG. 1, operation of the system begins when the collection operator inserts analyzer switch assembly 20 into the opening of customer receptacle 40 containing liquid 42 fully immersing probe 29. If the gravity of liquid 42 is within the appropriate specific gravity limits, float 26 will rise up bore 24 to a position close to proximity sensor 32 wherein the metal element of float 26 will cause proximity sensor 32 to send a signal to relay 36, close gate 37 and complete the circuit to timer 44. Operating for a preset duration, such as 20 seconds in a preferred embodiment, timer 44 activates pump 54. Pump 54 withdraws liquid 42 from container 40 through conduit 22 and into holding tank 50. If low gravity float 26 is still within a preset position close to sensor 32 when the timing cycle has lapsed, the completed circuit will restart timer 44 and continue pumping liquid 42 until either container 40 is empty or holding tank 50 fills to level sufficient to trip floatation switch 60 and deactivate pump 54.

If the gravity of the oil is higher than the upper specific gravity limit, float 28 will also rise in bore 25, causing proximity sensor 34 to send a signal to relay 38 and open gate 39. In this situation, signals from sensors 32, 34 have each caused relays 36, 38 to change the position of gates 37, 39, keeping the gates in opposite positions from those shown in FIG. 4 so that the circuit remains open and timer 44 is not activated.

It will be understood and appreciated that several options to transfer liquid 52 from holding tank 50 are available to the owner or operator of the system. As depicted in FIG. 1, a preferred embodiment optionally provides suction conduit 58 and discharge pump 54 used to transfer liquid 52 to another receptacle, transport or other holding device. Alternatively, pumps 54, 56 may be replaced by a single pump capable of serving the dual functions of pumps 54, 56 by use of valves to change its configuration. In another embodiment, the transport or other holding device may include a self-contained withdrawal pump system. In an other preferred embodiment, atmospheric vent 64 is provided if desired.

Through the system and method disclosed herein, it is now possible for an owner or operator of a used oil collection center to identify unadulterated recyclable motor oil and safely mix it with previously collected oil, for environmentally safe storage until transference from the holding tank to a recycling center for reclamation and refinement into useful lubricants or petroleum products.

Although the invention has been described herein in relation to its preferred embodiments, other alterations and modifications of the invention will become apparent to those of ordinary sill in the art upon reading the present disclosure, and it is intended that the scope of the invention disclosed herein be limited only by the broadest interpretation of the claims to which the inventors are legally entitled.

We claim:

1. A system comprising:
   a. means for determining whether a fluid in a receptacle has a specific gravity falling within a predetermined range;
   b. a holding tank;
   c. a conduit providing communication between the receptacle and holding tank;
   d. a pump adapted to transfer fluid through the conduit; and
   e. means for selectively activating the pump for a predetermined interval to transfer the fluid exhibiting a specific gravity within the predetermined range from the receptacle into the holding tank.

2. The system of claim 1 further comprising a timer means to control the pumping interval.

3. The system of claim 1 wherein the holding tank comprises a cover and an atmospheric ventilation apparatus.

4. The system of claim further comprising means for transferring the liquid from the holding tank to another receptacle.

5. The system of claim 1 wherein the means for determining whether the liquid has a specific gravity falling within a predetermined range comprises an analyzer switch assembly.

6. The system of claim 1 further comprising a means to deactivate the pump once the holding tank is full.

7. The system of claim 6 wherein the means for deactivating the pump once the holding tank is full comprises a float switch assembly.

8. The system of claim 5 wherein the analyzer switch assembly comprises a plurality of proximity switches and float members.

9. The system of claim 8 wherein the float members comprise a metallic conducting material.

10. The system of claim 9 wherein the low gravity float rises and floats in motor oil with an API gravity about 24 degrees and the high gravity float rises and floats in motor oil with an API gravity about 27.5 degrees.

11. The system of claim 8 wherein the float members further comprise low and high gravity floats.

12. The system of claim 11 wherein the low and high gravity floats rise and float in the liquid that has a specific gravity about equal to the minimum and maximum limits of the predetermined range.

13. A method for analyzing and collecting a liquid comprising the steps of:
   a. inserting a gravity probe into a receptacle of the liquid;
   b. determining whether the liquid in the receptacle has a specific gravity falling within a predetermined range; and
   c. selectively activating a pump cycle for transferring the liquid exhibiting a specific gravity within the predetermined range from the receptacle, through a conduit into a holding tank.

14. The method of claim 13 further comprising the step of using a timer to control the pump cycle.

15. The method of claim 13 further comprising the step of repeating the pump cycle until the receptacle is empty.

16. The method of claim 13 further comprising the step of deactivating the pump once the holding tank is full.

17. The method of claim 13 further comprising the step of transferring the liquid from the holding tank to another location.

* * * * *